(12) United States Patent
Sohn et al.

(10) Patent No.: US 7,863,448 B2
(45) Date of Patent: Jan. 4, 2011

(54) DYE FOR PHOTOELECTRONIC DEVICE, PHOTOANODE COMPRISING THE DYE AND PHOTOELECTRONIC DEVICE EMPLOYING THE PHOTOANODE

(75) Inventors: Byung Hee Sohn, Yongin-si (KR); Sang Cheol Park, Seoul (KR); Won Cheol Jung, Seoul (KR); Jung Gyu Nam, Yongin-si (KR); Young Jun Park, Suwon-si (KR); Eun Sung Lee, Seoul (KR)

(73) Assignee: Samsung Electronics Co., Ltd. (KR)

( * ) Notice: Subject to any disclaimer, the term of this patent is extended or adjusted under 35 U.S.C. 154(b) by 758 days.

(21) Appl. No.: 11/757,831

(22) Filed: Jun. 4, 2007

(65) Prior Publication Data

US 2008/0087325 A1 Apr. 17, 2008

(30) Foreign Application Priority Data

Aug. 22, 2006 (KR) .................. 10-2006-0079311

(51) Int. Cl.
*C07F 15/00* (2006.01)
*H01L 31/0256* (2006.01)

(52) U.S. Cl. .................. 546/10; 136/252; 136/243; 313/504

(58) Field of Classification Search ............ 136/252, 136/243; 546/10; 313/504
See application file for complete search history.

(56) References Cited

U.S. PATENT DOCUMENTS 7,626,115 B2 * 12/2009 Lee et al. .................... 136/252

OTHER PUBLICATIONS

DOI: 10.1002/chem.200305408;"Supramolecular Control of Charge-Transfer Dynamics on Dye-sensitized Nanocrystalline TiO2 Films"; Chem. Eur. J, 2004 vol. 10, pp. 595-602.
DOI: 10.1002/chem.200305408;"Supramolecular Control of Charge-Transfer Dynamics on Dye-sensitized Nanocrystalline TiO2 Films"; Chem. Eur. J, 2004 vol. 10, pp. 595-602.
Brian O'Regan, and Michael Gratzel, "A Low-Cost, High Efficiency Solar Cell Based on Dye-Sensitized Colloidal TiO2 Films," 353 Nature 737-739, Oct. 24, 1991.

* cited by examiner

*Primary Examiner*—Charanjit S Aulakh
(74) *Attorney, Agent, or Firm*—Cantor Colburn LLP

(57) ABSTRACT

Disclosed is a novel dye for use in a photoelectronic device, wherein the photoelectronic device is comprised of a photoanode comprising the dye. According to the novel dye, the dye is derived through the introduction of a group which narrows the dihedral angle of the dye ligand as well as through the introduction of conjugated groups. Since the dye has improved light sensitivity and absorption properties, it can be used to fabricate a photoelectronic device with high power conversion efficiency.

12 Claims, 4 Drawing Sheets

DYE FOR PHOTOELECTRONIC DEVICE, PHOTOANODE COMPRISING THE DYE AND PHOTOELECTRONIC DEVICE EMPLOYING THE PHOTOANODE

CROSS-REFERENCE TO RELATED PATENT APPLICATION

This non-provisional application claims priority to Korean Patent Application No. 10-2006-0079311, filed on Aug. 22, 2006, and all the benefits accruing therefrom under 35 U.S.C. §119, the content of which in its entirety is hereby incorporated by reference.

BACKGROUND OF THE INVENTION

1. Field of the Invention

The present invention relates to a novel dye for use in a photoelectronic device, wherein the photoelectronic device is comprised of a photoanode comprising the dye. More specifically, the present invention relates to a novel dye for use in a photoelectronic device in which the dye is derived through the introduction of a group that narrows the dihedral angle of the dye ligand as well as the introduction of conjugated groups. The resulting novel dye has increased light sensitivity and absorption efficiency.

2. Description of the Related Art

In recent years, numerous studies have focused on various alternative energy sources for conventional fossil fuels in an attempt to solve energy consumption problems. In particular, extensive research into the effective utilization of natural energy resources, including wind power, atomic energy and solar energy, have been conducted in an effort to identify alternative resources capable of replacing petroleum resources that may be used up within the next several decades.

Unlike other energy sources, solar cells utilize inexhaustible solar energy, and are environmentally friendly. Since the development of the first selenium (Se) solar cell in 1983, solar cells have elicited a great deal of attention and interest.

Many materials have been proposed as candidates for solar cells. Silicon is currently used in most commercially available solar cells. However, since silicon solar cells are expensive to manufacture, there are some limitations in regards to the practical application of the cells and the improvement in the efficiency of the cells. In an effort to overcome these limitations, the development of dye-sensitized solar cells that can be fabricated at reduced costs is currently ongoing.

Unlike silicon solar cells, dye-sensitized solar cells are photoelectrochemical solar cells that are comprised of photosensitive dye molecules capable of absorbing visible wavelengths to form electron-hole pairs, and a transition metal oxide for transferring the generated electrons. Various dye-sensitized solar cells have hitherto been developed. Of these, a representative dye-sensitized solar cell was reported by Grätzel et al. in Switzerland in 1991 (*Nature*, 1991, vol. 353, pp 737-740). The solar cell developed by Grätzel et al. comprises a photoanode comprising titanium dioxide nanoparticles covered with dye molecules, a platinum electrode as a cathode, and an electrolyte filler between the electrodes. Since this solar cell can be fabricated at a low cost relative to the electric power generated, it has received a great deal of attention as a potential replacement for conventional solar cells.

The structure of a conventional dye-sensitized solar cell is shown in FIG. 1. Referring to FIG. 1, the dye-sensitized solar cell comprises a photoanode 107, comprising a transparent electrode 101 and a light-absorbing layer 104, an electrolyte 102, and a cathode 103, wherein the light-absorbing layer is generally comprised of a metal oxide 105 and a dye 106.

The dye 106 may be in a neutral state (S), a transition state (S*), or an ionic state (S$^+$). When sunlight is incident on the dye, the dye molecules undergo an electronic transition from the ground state (S/S$^+$) to the excited state (S*/S$^+$) resulting in the formation of electron-hole pairs. The electrons in an excited state are injected into a conduction band (CB) of the metal oxide 105 resulting in the generation of an electromotive force.

As such, the performance of dye-sensitized solar cells is largely dependent on the light sensitivity and absorption efficiency of the dye(s). Thus, continuous efforts have been made in the field of dye-sensitized solar cells to develop a new dye that exhibits improved absorption properties and increased absorption efficiency for sunlight. For example, Narukuni Hirata et al. have reported the N845 Dye whose structure is chemically modified by the addition of a secondary electron donor moiety, N,N-(di-p-anisylamino)phenoxymethyl (*Chem. Eur. J.*, 2004, Vol. 10, pp. 595-602). However, there is still an unmet need in the art to develop a dye that exhibits improved absorption properties.

SUMMARY OF THE INVENTION

In one embodiment, the present invention provides a novel dye for use in a photoelectronic device that has good sensitivity to sunlight, and absorbs sunlight at a broad range of wavelengths, resulting in improved light absorption efficiency.

In another embodiment, the present invention provides a photoanode with high power conversion efficiency, which comprises the dye.

In yet another embodiment, the present invention provides a photoelectronic device, with high power conversion efficiency, comprising the photoanode.

In accordance with one aspect of the present invention, there is provided a dye for use in a photoelectronic device, represented by Formula 1 below:

[Formula 1]

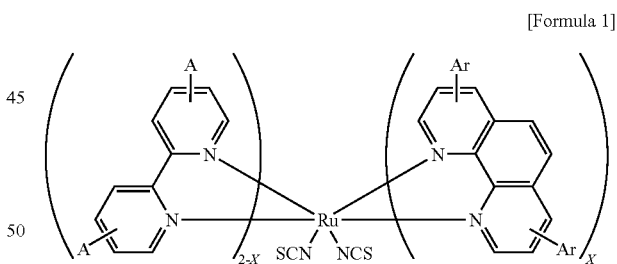

In Formula 1, each Ar, is independently selected from the group consisting of substituted and unsubstituted $C_4$-$C_{50}$ aryl, substituted and unsubstituted $C_2$-$C_{50}$ heteroaryl, substituted and unsubstituted $C_3$-$C_{30}$ cycloalkenyl, substituted and unsubstituted $C_2$-$C_{30}$ heterocycloalkenyl, substituted and unsubstituted $C_8$-$C_{30}$ arylalkenyl, and substituted and unsubstituted $C_6$-$C_{30}$ heteroarylalkenyl groups; A is a carboxyl group, a phosphate group or a salt thereof; and X is about 1 or about 2, provided that when X is about 2, at least one Ar includes at least one or more substituents selected from the group consisting of a carboxyl group, a phosphate group and salts thereof.

In one embodiment of the present invention, in Formula 1, each Ar may be independently selected from at least one of the group consisting of cyclopropene, cyclobutadiene, cyclopentadiene, cycloheptatriene, cyclooctatetraene, benzene, biphenyl, naphthalene, azulene, pyrene, benzopyrene, dibenzopyrene, phenanthroline, pyrrole, pyridine, pyrimidine, purine, furan, thiophene, thymine, pyridone, pyrane, anthracene, phenanthrene, quinoline, indole, benzothiophene, oxadiazole, imidazole, triazole and vinylenephenylene which may be unsubstituted or substituted with at least one substituent selected from a carboxyl group and its salts, a phosphate group and its salts, and $C_1$-$C_{30}$ alkoxy groups.

In another embodiment there is provided a photoanode comprising a transparent electrode, a metal oxide layer formed on the transparent electrode, and the dye adsorbed on the metal oxide layer.

In yet another embodiment there is provided a photoelectronic device comprising the photoanode, a cathode, and an electrolyte layer formed between the photoanode and the cathode.

BRIEF DESCRIPTION OF THE DRAWINGS

The aforementioned features and other advantages of the present invention will be more clearly understood from the following detailed description taken in conjunction with the accompanying drawings, in which.

DESCRIPTION OF THE PREFERRED EMBODIMENTS

Figure 1:
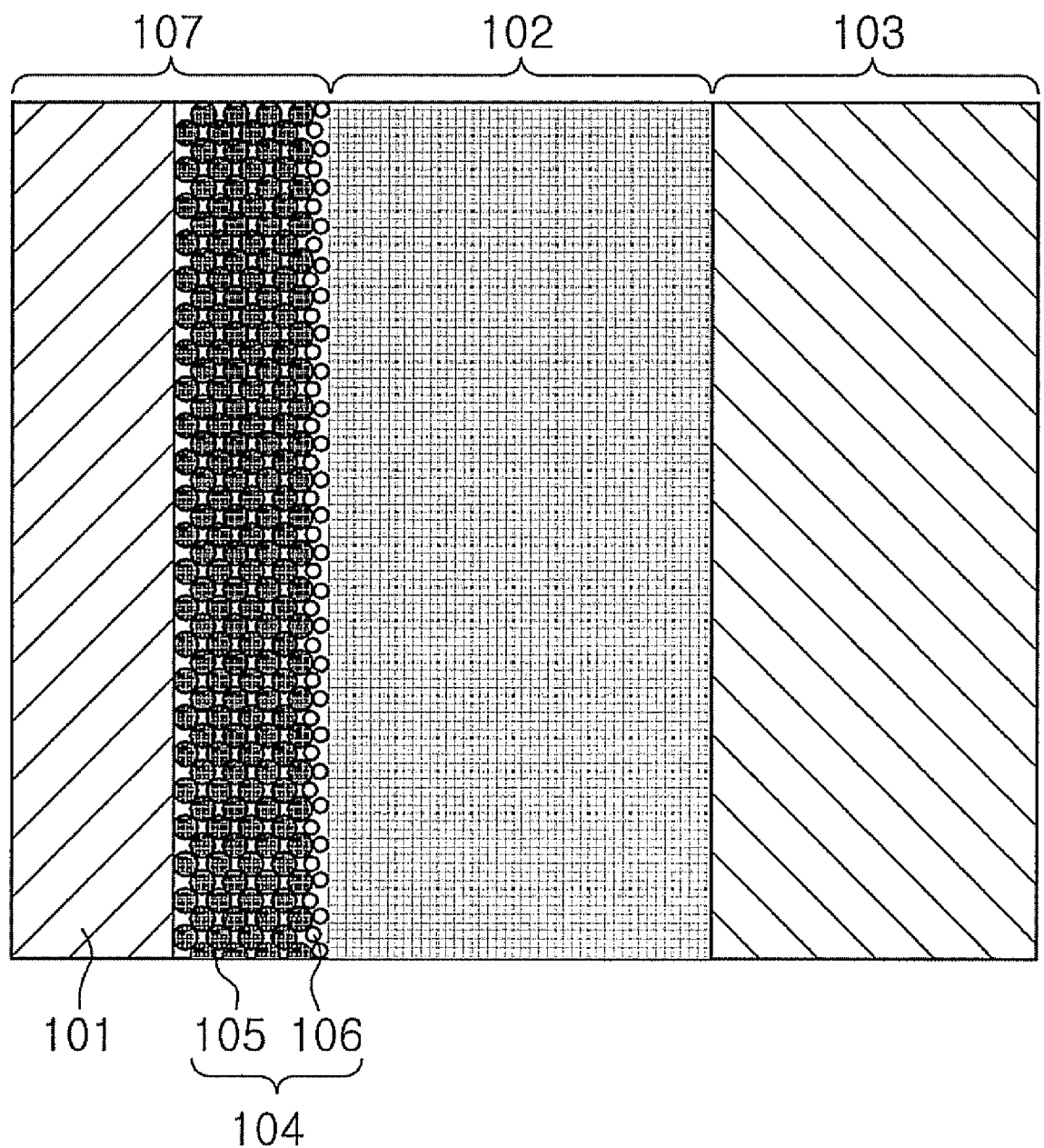
FIG. 1 is an exemplary embodiment that schematically shows a cross-sectional view of a conventional photoelectronic device (solar cell)

Hereinafter, exemplary embodiments of the present invention will be explained in greater detail with reference to the accompanying drawings.

In one embodiment, the present invention provides a novel dye for use in a photoelectronic device. The dye of the present invention may be represented by Formula 1 below:

[Formula 1]

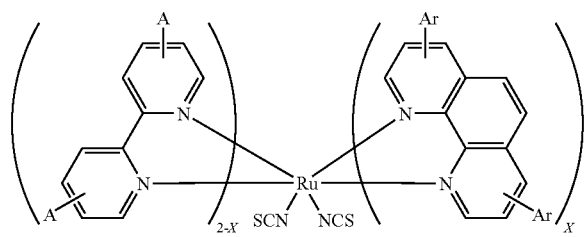

In Formula 1 each Ar, is independently selected from at least one of the group consisting of substituted and unsubstituted $C_4$-$C_{50}$ aryl, substituted and unsubstituted $C_2$-$C_{50}$ heteroaryl, substituted and unsubstituted $C_3$-$C_{30}$ cycloalkenyl, substituted and unsubstituted $C_2$-$C_{30}$ heterocycloalkenyl, substituted and unsubstituted $C_8$-$C_{30}$ arylalkenyl, and substituted and unsubstituted $C_6$-$C_{30}$ heteroarylalkenyl groups; A is a carboxyl group, a phosphate group or a salt thereof; and X is about 1 or about 2, provided that when X is about 2, at least one Ar includes at least one substituent selected from the group consisting of a carboxyl group, a phosphate group and salts thereof.

As is apparent from the structure of Formula 1, a group was introduced (i.e., vinyl) into the bipyridyl ligand which narrows the dihedral angle between the two pyridyl rings. In addition, conjugated aromatic groups were also introduced into the bipyridyl ligand. The presence of these groups allows the dye to have an extended pi-conjugated system and rich $\pi$ (pi) electrons, thus causing a red shift in the light absorption region of the dye toward a longer wavelength region, which is close to the strong intensity region in the spectrum of sunlight. Therefore, the dye exhibits increased light absorption efficiency as compared to dyes that are conventionally used in photoelectronic devices.

In another embodiment, in Formula 1, each Ar may be independently selected from at least one of the group consisting of substituted and unsubstituted $C_4$-$C_{30}$ aryl, substituted and unsubstituted $C_2$-$C_{30}$ heteroaryl, substituted and unsubstituted $C_3$-$C_{10}$ cycloalkenyl, substituted and unsubstituted $C_2$-$C_{10}$ heterocycloalkenyl, substituted and unsubstituted $C_8$-$C_{20}$ arylalkenyl, and substituted and unsubstituted $C_6$-$C_{20}$ heteroarylalkenyl groups.

In yet another embodiment, in Formula 1, each Ar may be substituted with a substituent selected from the group consisting of a carboxyl group and its salts, a phosphate group and its salts, nitro, amino, cyano, hydrazine, hydrazone, halogen, $C_1$-$C_{30}$ alkyl, $C_1$-$C_{30}$ hydroxyalkyl, $C_1$-$C_{30}$ alkoxy, $C_1$-$C_{30}$ alkoxyalkyl, $C_6$-$C_{30}$ aryl, $C_6$-$C_{30}$ arylalkyl, $C_6$-$C_{30}$ aryloxy, $C_2$-$C_{30}$ heteroaryl, $C_2$-$C_{30}$ heteroarylalkyl, $C_2$-$C_{30}$ heteroaryloxy, $C_5$-$C_{20}$ cycloalkyl, $C_2$-$C_{30}$ heterocycloalkyl, $C_1$-$C_{30}$ alkyl ester, $C_1$-$C_{30}$ heteroalkyl ester, $C_6$-$C_{30}$ aryl ester, $C_2$-$C_{30}$ heteroaryl ester, and one or more of the foregoing substituents.

Taking into consideration the adsorption of the dye to metal oxides, each Ar is preferably substituted with at least one substituent selected from the group consisting of a carboxyl group and its salts, a phosphoric acid group and its salts, alkyl ester, heteroalkyl ester, aryl ester, heteroaryl ester, and $C_1$-$C_{30}$ alkoxy. More preferably, each Ar is substituted with at least one substituent selected from at least one of the group consisting of a carboxyl group and its salts, a phosphoric acid group and its salts, and $C_1$-$C_{30}$ alkoxy groups.

Specifically, each Ar may independently be selected from at least one of the group consisting of cyclopropene, cyclobutadiene, cyclopentadiene, cycloheptatriene, cyclooctatetraene, benzene, biphenyl, naphthalene, azulene, pyrene, benzopyrene, dibenzopyrene, phenanthroline, pyrrole, pyridine, pyrimidine, purine, furan, thiophene, thymine, pyridone, pyrane, anthracene, phenanthrene, quinoline, indole, benzothiophene, oxadiazole, imidazole, triazole or vinylenephenylene, which is unsubstituted or substituted with at least one substituent selected from a carboxyl group and its salts, a phosphate group and its salts, and $C_1$-$C_{30}$ alkoxy groups.

In one embodiment, suitable examples of the dye include at least one selected from the group consisting of the compounds represented by Formulas 2, 3, 4, 5, 6, and 7:

[Formula 2]
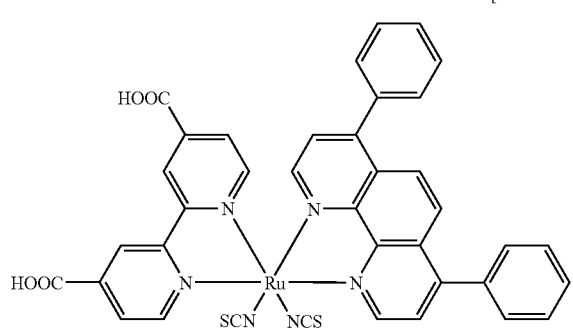
[Formula 3]
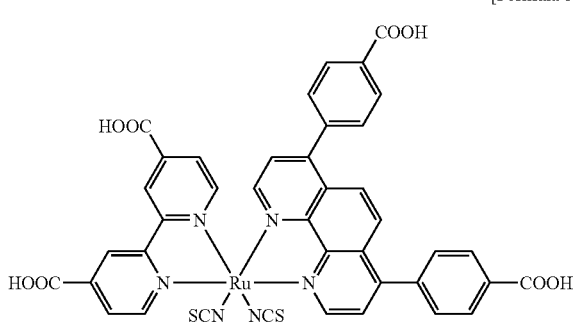
[Formula 4]
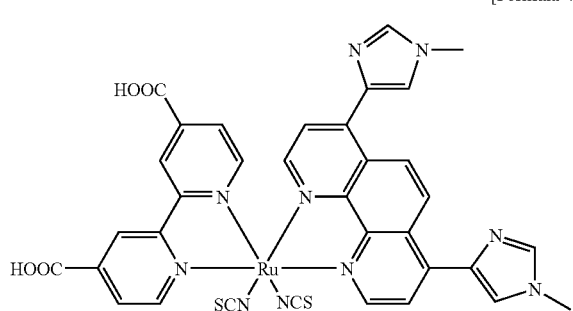
[Formula 5]
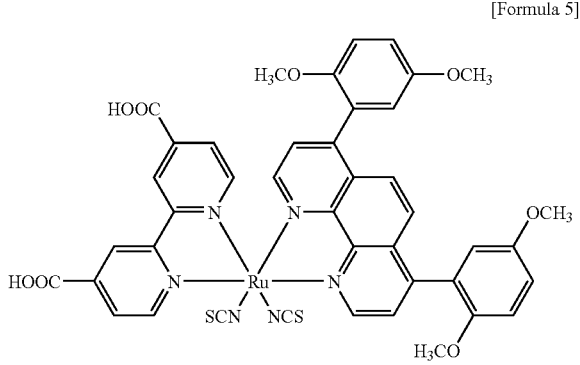
-continued
[Formula 6]
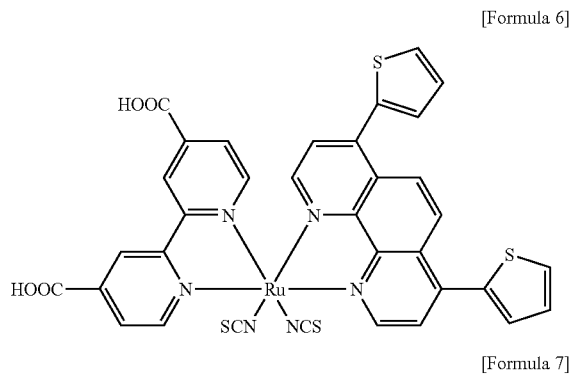
[Formula 7]
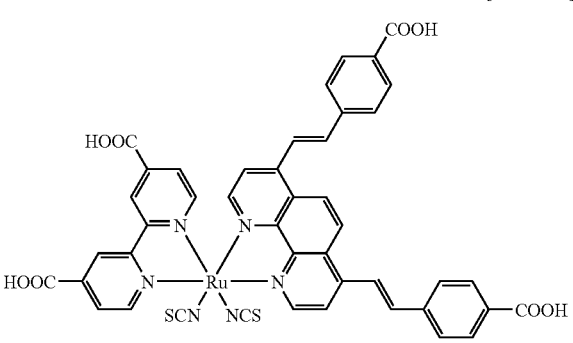
The dye of the present invention may be prepared by any synthesis method generally known in the art. Preferably, the dye can be synthesized by Reaction schemes 1 or 2 as follows:
Reaction Scheme 1
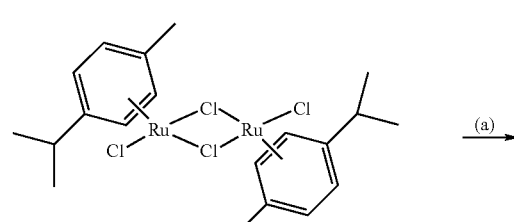
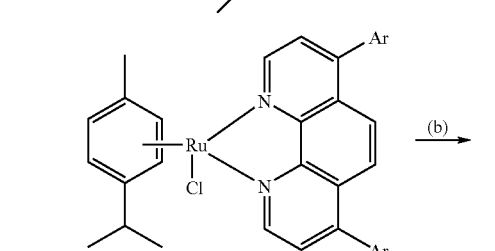
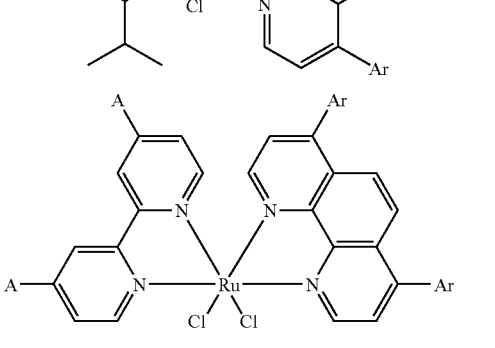

-continued

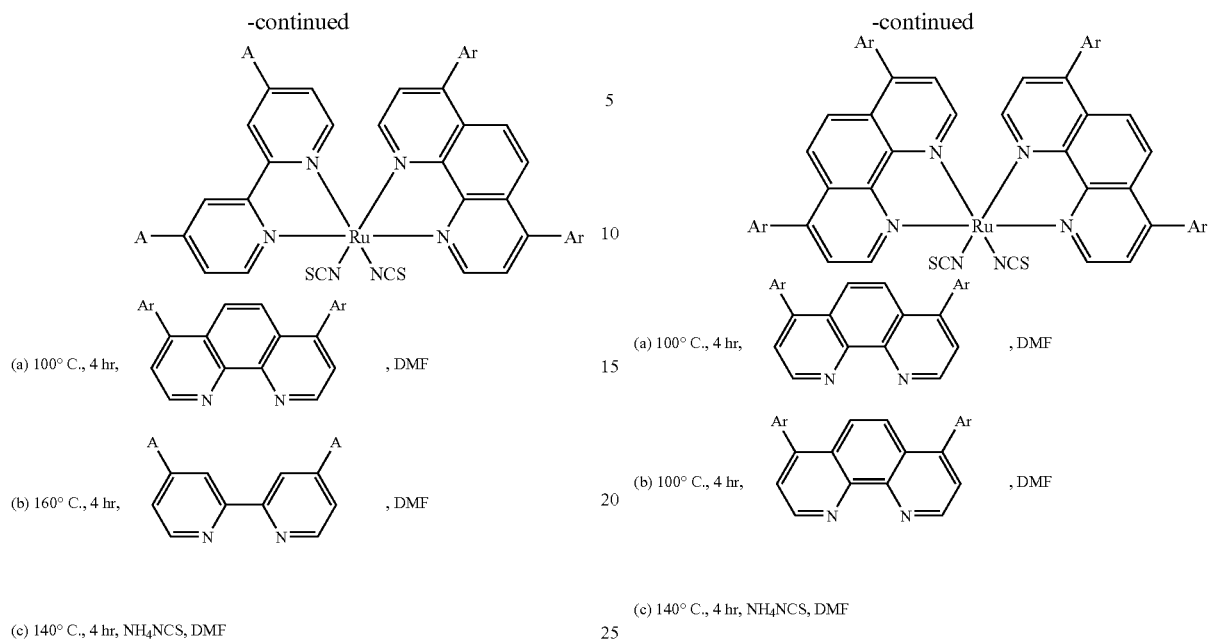

In Reaction Scheme 1, each Ar is selected from at least one of the group consisting of substituted and unsubstituted $C_4$-$C_{50}$ aryl, substituted and unsubstituted $C_2$-$C_{50}$ heteroaryl, substituted and unsubstituted $C_3$-$C_{30}$ cycloalkenyl, substituted and unsubstituted $C_2$-$C_{30}$ heterocycloalkenyl, substituted and unsubstituted $C_8$-$C_{30}$ arylalkenyl, and substituted and unsubstituted $C_6$-$C_{30}$ heteroarylalkenyl; and A is a carboxyl group, a phosphate group or a salt thereof;

Reaction Scheme 2

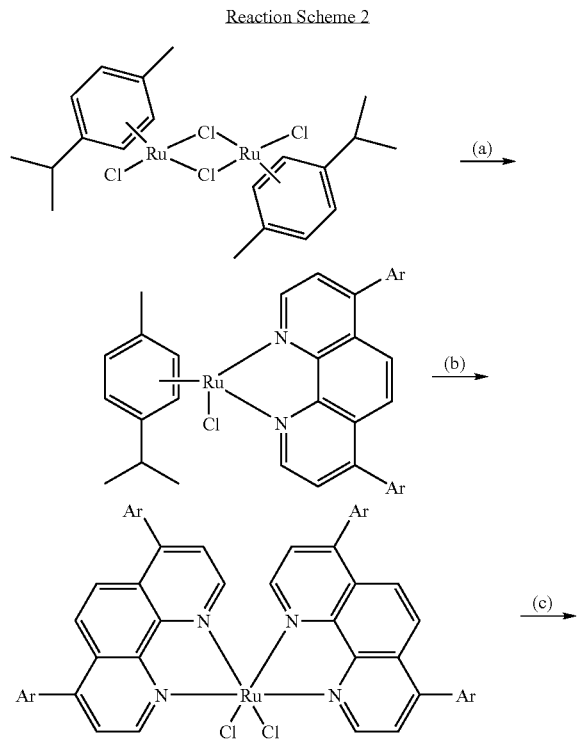

In Reaction Scheme 2, each Ar is selected from at least one of the group consisting of substituted and unsubstituted $C_4$-$C_{50}$ aryl, substituted and unsubstituted $C_2$-$C_{50}$ heteroaryl, substituted and unsubstituted $C_3$-$C_{30}$ cycloalkenyl, substituted and unsubstituted $C_2$-$C_{30}$ heterocycloalkenyl, substituted and unsubstituted $C_8$-$C_{30}$ arylalkenyl, and substituted and unsubstituted $C_6$-$C_{30}$ heteroarylalkenyl, with the proviso that at least one Ar includes at least one substituent selected from a carboxyl group, a phosphate group and salts thereof.

Examples of suitable organic solvents that can be used in the reactions include at least one more selected from the group consisting of dimethylformamide (DMF), toluene, dichloromethane ($CH_2Cl_2$), triethylamine, dimethoxy ether, tetrahydrofuran, and a combination of one or more of the foregoing organic solvents. Although the dichloro(p-cymene) ruthenium(II) dimer is used as a starting material for the dye of the present invention, any material that is generally used in the field of photoelectronic devices may be used without any limitation. Ruthenium compounds, such as N3 Dye, N719 Dye and Black Dye, are preferably used. The reactions are preferably conducted under a nitrogen atmosphere at about 70 to about 200° C. for about 1 to about 12 hours.

According to one embodiment, the present invention also provides a photoanode comprising the dye of Formula 1. Specifically, the photoanode of the present invention comprises a transparent electrode, a metal oxide layer formed on the transparent electrode, and the dye of Formula 1 adsorbed on the metal oxide layer.

According to another embodiment, for better conductivity, it is preferred that the transparent electrode be a transparent substrate coated with an electrically conductive material. The substrate may be of any type so long as it is transparent. Specific examples of transparent substrates include, one or more selected from the group consisting of transparent inorganic substrates, such as quartz and glass, and transparent plastic substrates, such as polyethylene terephthalate ("PET"), polyethylene naphthalate ("PEN"), polycarbonate, polystyrene, polypropylene, polymethylmethacrylate, and the like; and a combination comprising at least one of the foregoing transparent substrates. Examples of suitable conductive materials coated on the substrate include, one or more selected from the group consisting of indium tin oxide (ITO), fluorine-doped tin oxide (FTO), ZnO—Ga$_2$O$_3$, ZnO—Al$_2$O$_3$, SnO$_2$—Sb$_2$O$_3$, and a combination of one or more of the foregoing conductive materials.

According to yet another embodiment, the metal oxide layer can be formed of at least one metal oxide selected from one or more of the group consisting of titanium, niobium, hafnium, indium, tin, and zinc oxides, and a combination comprising at least one of the foregoing metal oxides. These metal oxides may be used alone or in combination thereof. Titanium oxide (TiO$_2$) can be preferably used. The application of the metal oxide can be performed using a general coating technique, such as screen printing or spin coating.

In accordance with one aspect of the present invention the photoanode can be produced by a method already known in the field of photoelectronic devices. For example, the photoanode of the present invention is produced by the following procedure. First, a porous metal oxide is applied to a transparent substrate coated with an electrically conductive material, followed by baking to form a metal oxide layer. Second, the resulting structure is coated with a solution containing the dye of Formula 1 for a specified time in order to allow the dye to adsorb on the surface of the metal oxide layer.

Since the photoanode of the present invention uses the dye of Formula 1 with improved light sensitivity and absorption properties, the photoanode exhibits improved light absorption efficiency and higher power conversion efficiency as compared to photoanodes using conventional dyes.

In accordance with another aspect, the present invention also provides a photoelectronic device comprising the photoanode, a cathode, and an electrolyte layer formed between the photoanode and the cathode.

According to one embodiment, the cathode may be formed from any electrically conductive material. The cathode may also be made of an insulating material and as long as the conductive layer is disposed on the surface of the cathode facing the photoanode, any insulating material may be used to form the cathode. As such, the electrode must be formed using electrochemically stable material, in particular, platinum, gold, carbon, or carbon nanotubes.

For the purpose of improving the catalytic effects of oxidation and reduction, it is preferred that the surface of the cathode facing the photoanode comprise a microstructure with an increased surface area. For example, the cathode is preferably made of platinum black or porous carbon. The platinum black cathode can be produced by anodic oxidation of platinum, treatment with hexachloroplatinate, or the like. The porous carbon cathode can be produced by sintering of fine carbon particles or baking of an organic polymer.

According to another embodiment, any electrolyte solution may be used to form the electrolyte layer so long as it exhibits hole conductivity. Suitable examples of an electrolyte solution include one or more selected from the group consisting of a solution of iodine in acetonitrile, an N-methyl-2-pyrrolidone (NMP) solution, 3-methoxypropionitrile and a combination of one or more of the foregoing solutions.

According to yet another embodiment, the photoelectronic device of the present invention can be fabricated by any method known in the art.

Hereinafter, preferred embodiments of the present invention will be explained in more detail with reference to the following examples. However, these examples are merely set forth to illustrate the invention and are not to be construed as limiting the scope of the invention.

EXAMPLES

Synthesis Example 1

Synthesis of the Dye

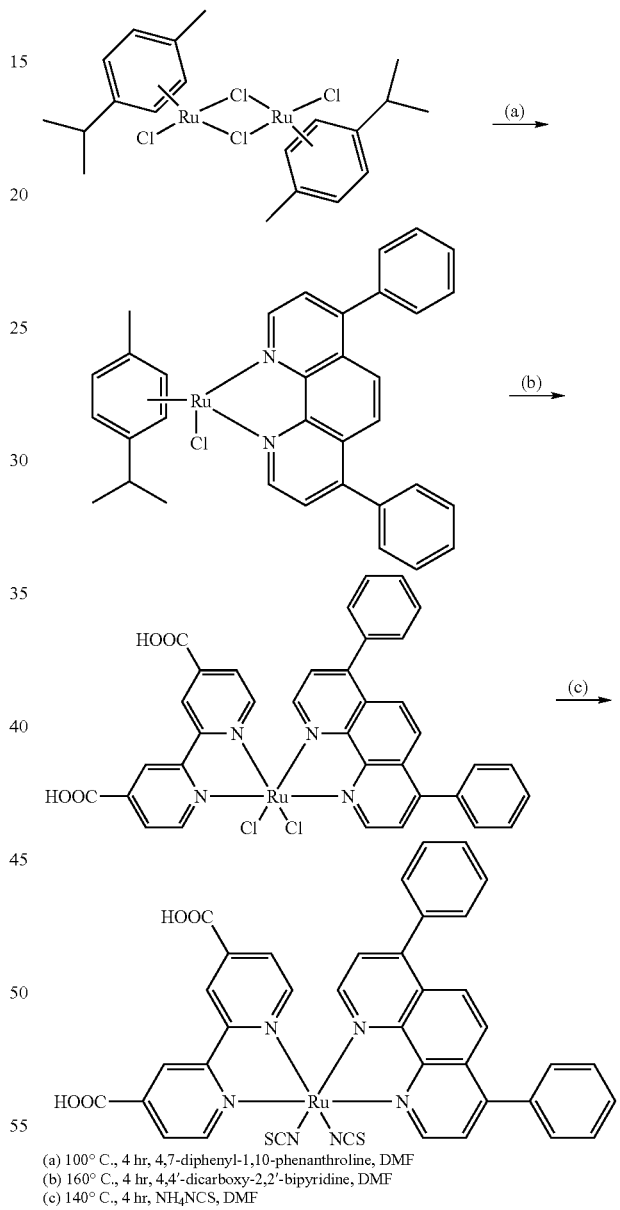

Reaction Scheme 3

(a) 100° C., 4 hr, 4,7-diphenyl-1,10-phenanthroline, DMF
(b) 160° C., 4 hr, 4,4'-dicarboxy-2,2'-bipyridine, DMF
(c) 140° C., 4 hr, NH$_4$NCS, DMF A solution of 4,7-Diphenyl-1,10-phenanthroline (266 mg, 0.8 mMol) and dichloro(p-cymene)ruthenium(II) dimmer (240 mg, 0.2 mMol) in 50 ml (milliliters) of dimethylformamide ('DMF') was refluxed under a nitrogen atmosphere at 100° C. for 4 hours. After 4,4'-dicarboxy-2,2'-bipyridine (216 mg, 0.8 mmol) was added to the solution, the mixture was refluxed at 160° C. for 4 hours. Ammonium thiocyanate (NH$_4$NCS) (608 mg, 8 mmol) was added to the hot mixture and refluxed at 140° C. for 4 hours. Subsequently, the resulting mixture was allowed to cool to room temperature and the solvent was removed by distillation under reduced pressure to obtain a purple solid precipitate. The precipitate was added to 300 ml of water and dissolved by sonication for 5 minutes. The pH of the solution was adjusted to pH 4 by the addition of a 0.2 M nitric acid ($HNO_3$) solution. The acidic solution was subsequently allowed to stand in a freezer for one day to obtain a precipitate. The precipitate was washed sequentially with water and diethyl ether (×3), and then air-dried. The dried precipitate was loaded onto a column packed with sephadex LH-C20 to a height of 30 cm (centimeters), and then the column was eluted with methanol. The elute was collected and dried to give the final compound.

Evaluation of Characteristics of the Dye

Figure 2:
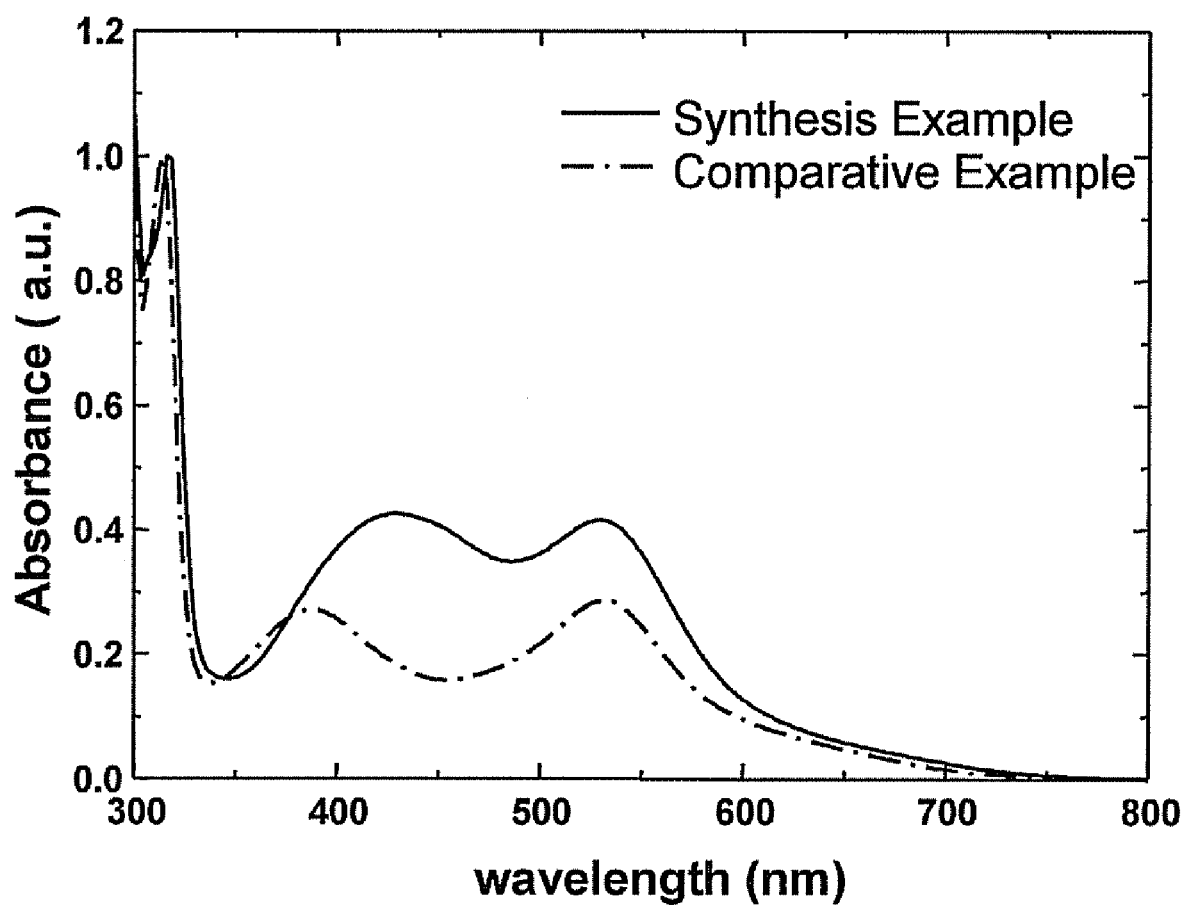
FIG. 2 is a graph comparing the absorbance of the dye prepared in Synthesis Example 1, with the absorbance of the N3 Dye.
Figure 3:
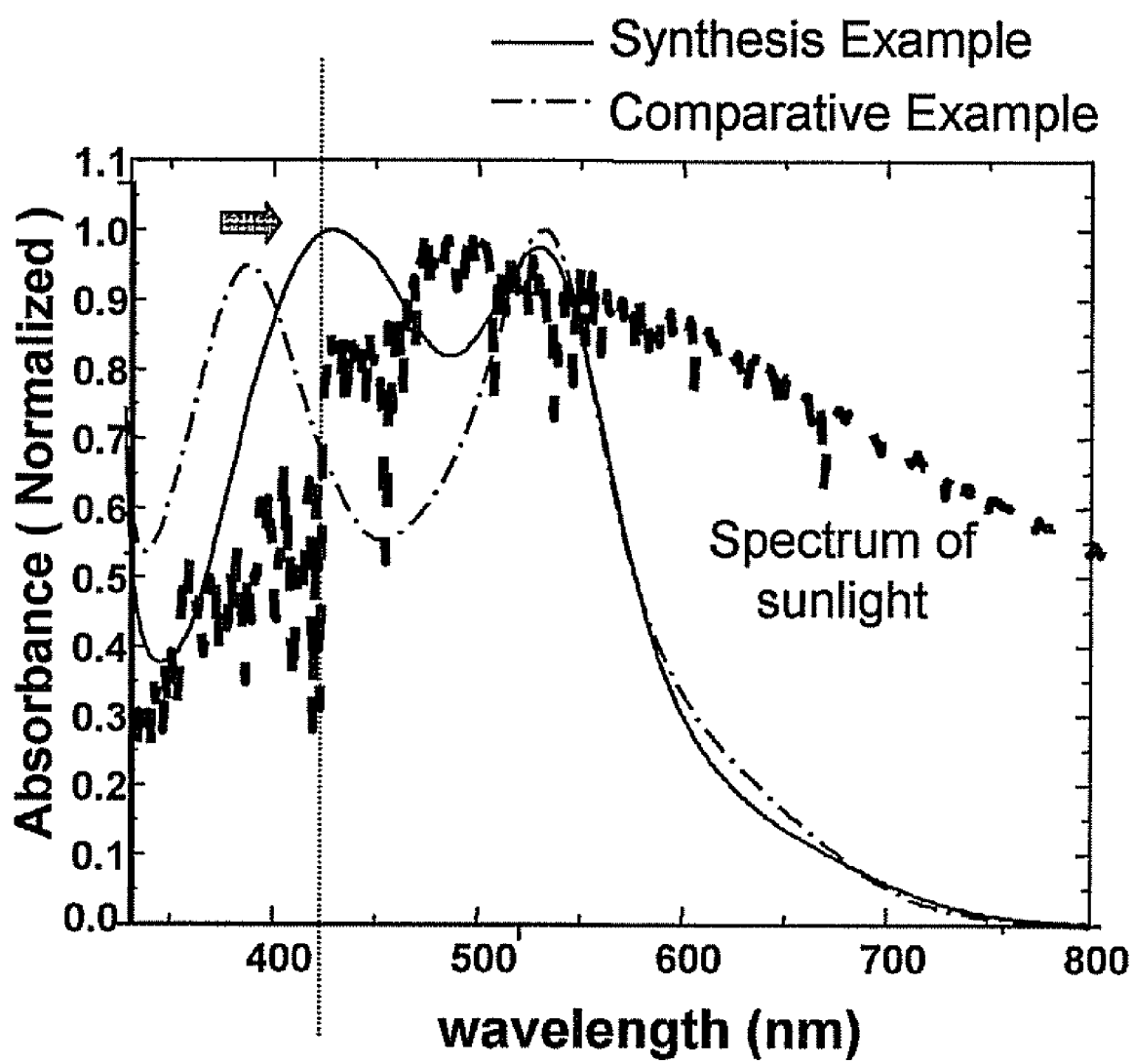
FIG. 3 shows the absorption spectra of the dye prepared in Synthesis Example 1, the N3 Dye and sunlight.

To evaluate the absorption properties of the dye prepared in Synthesis Example 1, the absorbance of the dye was measured by UV-Vis-spectroscopy (JASCO (V-560), Absorbance mode, Scanning speed: 400 nm/min.). The results are shown in FIG. 2. For comparison, the absorbance of the N3 Dye (Naz Chemical) was measured. FIG. 3 is a graph comparing the absorption spectra of the dye prepared in Synthesis Example 1, with the N3 Dye and with sunlight.

The graphs of FIGS. 2 and 3 reveal that the dye prepared in Synthesis Example 1 demonstrates increased absorption intensity and a broader absorption spectrum when compared to the N3 Dye. In addition, the graphs demonstrate that the strong intensity region and the absorption spectrum of the dye were consistent with the wavelength intensity region and the absorption spectrum of sunlight.

Example 1

Production of a Photoanode and Fabrication of a Photoelectronic Device

After fluorine-doped tin oxide (FTO) was applied to a glass substrate using a sputter coater, a paste of $TiO_2$ particles (particle diameter: 13 nm) was coated thereon by screen printing, and then baked at 450° C. for 30 minutes to form a porous $TiO_2$ film having a thickness of about 15 μm (micrometers). Subsequently, the glass substrate, on which the $TiO_2$ film was formed, was dipped in a 0.3 mM solution of the dye (Synthesis Example 1), prepared in a mixture of butanol and acetonitrile (1:1 (v/v)), for 24 hours and then dried to allow the dye to adsorb on the surface of the $TiO_2$ layer, thereby completing production of a photoanode.

Next, platinum was deposited on a glass substrate coated with indium tin oxide (ITO) using a sputter coater to form a platinum film, and thereafter, a fine hole for injection of an electrolyte was formed thereon using a drill (diameter: 0.75 mm) to produce a cathode.

The photoanode and the cathode were assembled using the following procedure. First, a polymer film (SURLYN, DuPont) having a thickness of about 40 μm was interposed between the two electrodes. The electrodes were adhered to each other under a pressure of about 1 to about 3 atm (atmospheres) on a hot plate at about 100 to about 140° C. As a result, the polymer was attached to the two electrodes by heat and pressure.

Next, an electrolyte solution was used to fill in the space formed between the two electrodes. The electrolyte solution was applied through the fine hole penetrating the cathode to complete fabrication of a photoelectronic device. An $I^{3-}/I^-$ electrolyte solution of 0.6 moles of 1,2-dimethyl-3-propyloctyl-imidazolium iodide, 0.2 moles of LiI, 0.04 moles of $I_2$ and 0.2 moles of 4-tert-butylpyridine (TBP) in acetonitrile was used as the electrolyte solution.

Evaluation of Characteristics of the Photoelectronic Device

Figure 4:
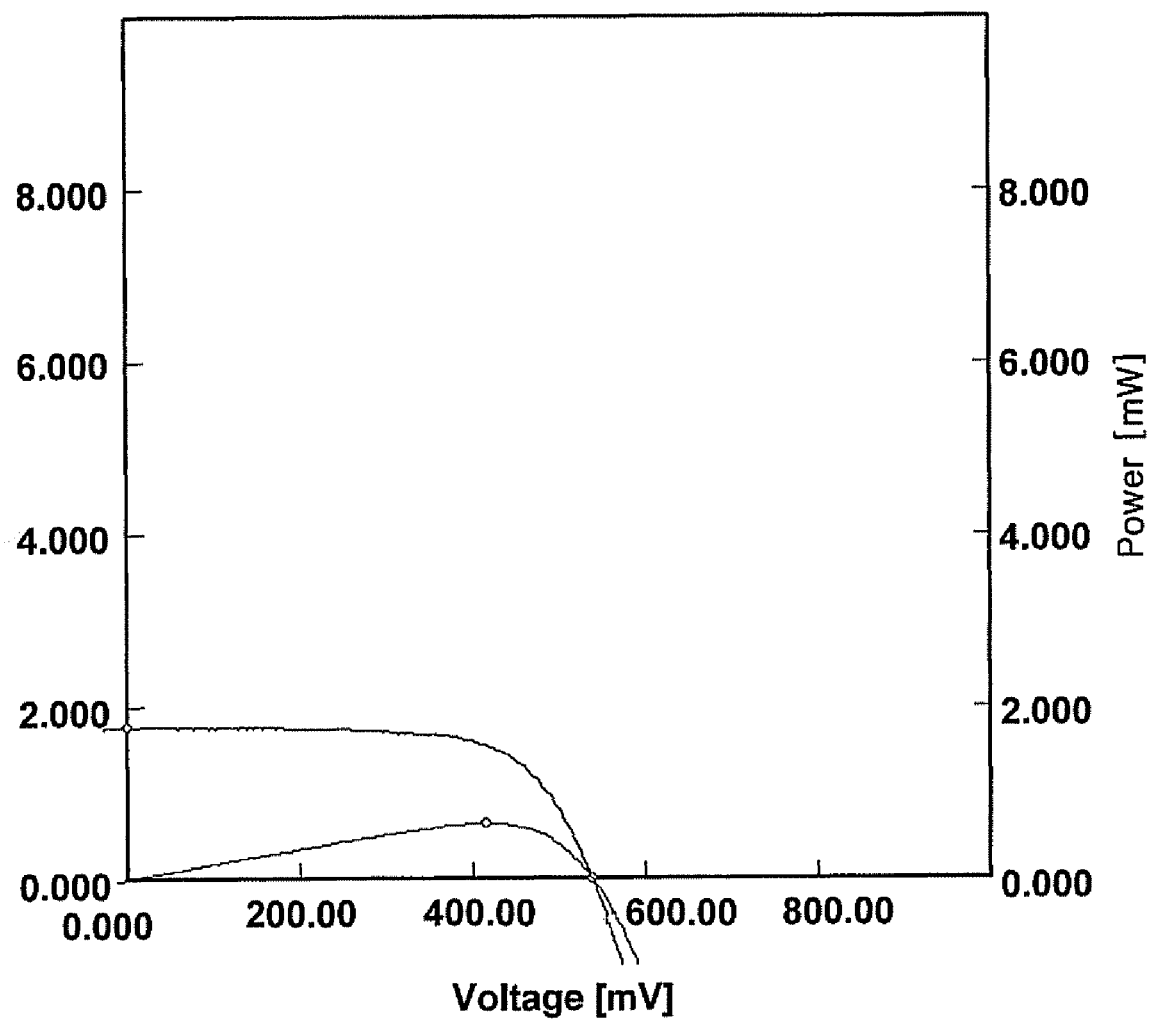
FIG. 4 is a graph showing the Voltage (current) transfer characteristics of the photoelectronic device fabricated in Example 1.

The photovoltage and the photocurrent of the device fabricated in Example 1 were measured to calculate the power conversion efficiency of the device. For the measurements, a xenon lamp (01193, Oriel) was used as a light source, and a standard solar cell (Fraunhofer Institute Solar Engeriessysteme, Certificate No. C-ISE369, Type of material: Mono-Si+ KG filter) was used to compensate for the solar conditions (AM 1.5) of the xenon lamp. The measured photocurrent-voltage curve is plotted in FIG. 4.

The photocurrent density ($I_{sc}$), voltage ($V_{oc}$) and fill factor (FF) of the device were determined from the photocurrent-voltage curve, and the power conversion efficiency ($\eta_e$) of the device was calculated according to Equation 1:

$$\eta e(\%) = (V_{oc} \cdot I_{sc} \cdot FF)/(P_{inc}) \text{ In Equation 1, } P_{inc} \text{ is 100 mw/cm}^2 \text{ (1 sun).} \quad \text{[Equation 1]}$$

The results are shown in Table 1.

TABLE 1

|  | $I_{sc}$ (mA) | $V_{oc}$ (mV) | FF | $\eta_e$ (%) |
| --- | --- | --- | --- | --- |
| Example 1 | 7.037 | 538.17 | 0.677 | 2.573 |

As can be seen from the results of Table 1, the photoanode comprising the dye of the present invention and the photoelectronic device employing the photoanode showed high power conversion efficiency.

As described herein, the dye of the present invention is derived through the introduction of a group which narrows the dihedral angle of the dye ligand as well as through the introduction of conjugated groups. Since the dye has good light sensitivity and improved light absorption properties, it can be used to produce a photoanode with high power conversion efficiency. In addition, a photoelectronic device comprising the photoanode has high power conversion efficiency.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A dye represented by Formula 1 below:

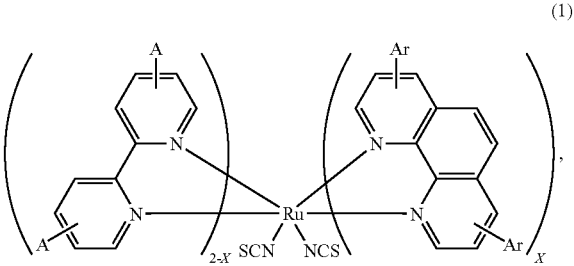

(1)

wherein each Ar is independently selected from the group consisting of substituted and unsubstituted $C_6$-$C_{50}$ aryl, substituted and unsubstituted $C_2$-$C_{50}$ heteroaryl, substituted and unsubstituted $C_3$-$C_{30}$ cycloalkenyl, substituted and unsubstituted $C_2$-$C_{30}$ heterocycloalkenyl, substituted and unsubstituted $C_8$-$C_{30}$ arylalkenyl, and substituted and unsubstituted $C_6$-$C_{30}$ heteroarylalkenyl groups; A is a carboxyl group, a phosphate group or a salt thereof; and X is 1 to 2, provided that when X is 2, at least one Ar includes at least one substituent selected from the group consisting of a carboxyl group, a phosphate group and salts thereof.

2. The dye according to claim 1, wherein each Ar is independently selected from the group consisting of substituted and unsubstituted $C_6$-$C_{30}$ aryl, substituted and unsubstituted $C_2$-$C_{30}$ heteroaryl, substituted and unsubstituted $C_3$-$C_{10}$ cycloalkenyl, substituted and unsubstituted $C_2$-$C_{10}$ heterocycloalkenyl, substituted and unsubstituted $C_8$-$C_{20}$ arylalkenyl, and substituted and unsubstituted $C_6$-$C_{20}$ heteroarylalkenyl groups.

3. The dye according to claim 1, wherein each Ar is substituted with a substituent selected from the group consisting of a carboxyl group and its salts, a phosphate group and its salts, nitro, amino, cyano, hydrazine, hydrazone, halogen, $C_1$-$C_{30}$ alkyl, $C_1$-$C_{30}$ hydroxyalkyl, $C_1$-$C_{30}$ alkoxy, $C_1$-$C_{30}$ alkoxyalkyl, $C_6$-$C_{30}$ aryl, $C_6$-$C_{30}$ arylalkyl, $C_6$-$C_{30}$ aryloxy, $C_2$-$C_{30}$ heteroaryl, $C_2$-$C_{30}$ heteroarylalkyl, $C_2$-$C_{30}$ heteroaryloxy, $C_5$-$C_{20}$ cycloalkyl, $C_2$-$C_{30}$ heterocycloalkyl, $C_1$-$C_{30}$ alkyl ester, $C_1$-$C_{30}$ heteroalkyl ester, $C_6$-$C_{30}$ aryl ester, $C_2$-$C_{30}$ heteroaryl ester, and a combination of one or more of the foregoing substituents.

4. The dye according to claim 1, wherein each Ar is substituted with a substituent selected from the group consisting of a carboxyl group and its salts, a phosphate group and its salts, and $C_1$-$C_{30}$ alkoxy groups.

5. The dye according to claim 1, wherein each Ar is independently selected from the group consisting of cyclopropene, cyclobutadiene, cyclopentadiene, cycloheptatriene, cyclooctatetraene, benzene, biphenyl, naphthalene, azulene, pyrene, benzopyrene, dibenzopyrene, phenanthroline, pyrrole, pyridine, pyrimidine, purine, furan, thiophene, thymine, pyridone, pyrane, anthracene, phenanthrene, quinoline, indole, benzothiophene, oxadiazole, imidazole, triazole and vinylenephenylene which is unsubstituted or substituted with at least one substituent selected from a carboxyl group and its salts, a phosphate group and its salts, and $C_1$-$C_{30}$ alkoxy groups.

6. The dye according to claim 1, wherein the dye is the compound represented by one of Formulas 2, 3, 4, 5, 6, or 7 below:

[Formula 2]

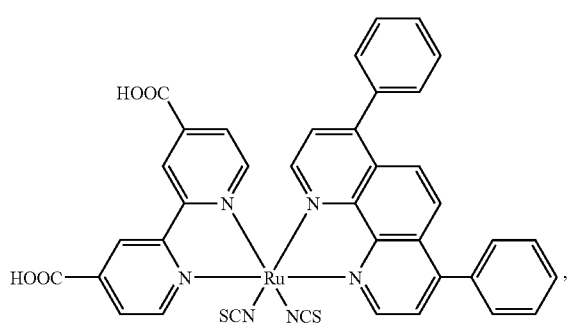

-continued

[Formula 3]

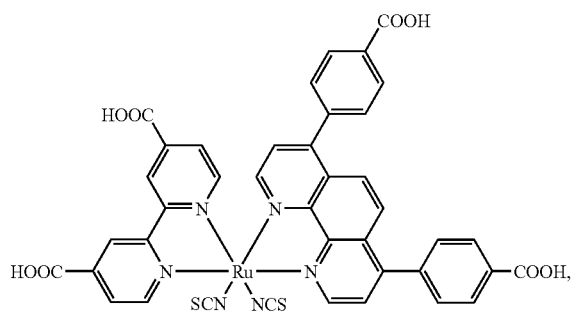

[Formula 4]

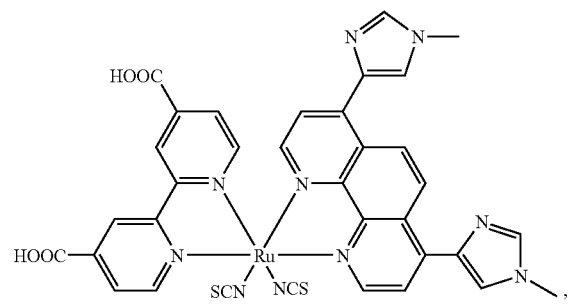

[Formula 5]

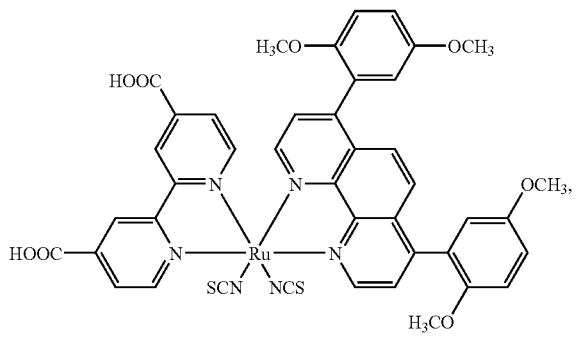

[Formula 6]

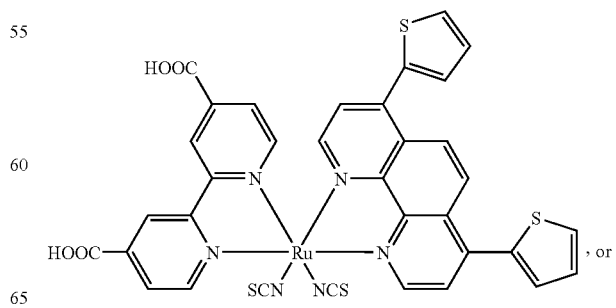

-continued

[Formula 7]

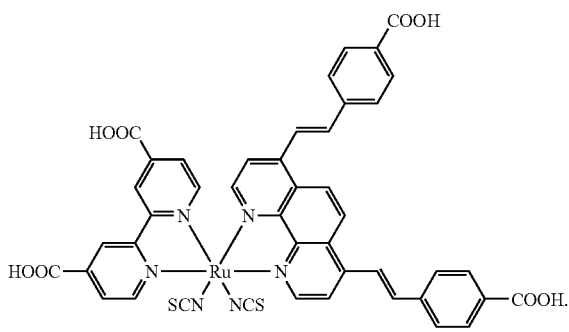

7. A photoanode comprising:
a transparent electrode;
a metal oxide layer formed on the transparent electrode; and
the dye according to claim 1 adsorbed on the metal oxide layer.

8. The photoanode according to claim 7, wherein the transparent electrode is a transparent substrate coated with an electrically conductive material.

9. The photoanode according to claim 8, wherein the transparent substrate is one or more selected from the group consisting of transparent inorganic substrates, such as quartz and glass, and transparent plastic substrates, such as polyethylene terephthalate, polyethylene naphthalate, polycarbonate, polystyrene, polypropylene, polymethylmethacrylate, and the like, and a combination comprising at least one of the foregoing transparent substrates.

10. The photoanode according to claim 8, wherein the conductive material is selected from the group consisting of indium tin oxide (ITO), fluorine-doped tin oxide (FTO), $ZnO\text{-}Ga_2O_3$, $ZnO\text{-}Al_2O_3$, $SnO_2\text{-}Sb_2O_3$, and a combination of one or more of the foregoing conductive materials.

11. The photoanode according to claim 7, wherein the metal oxide layer is formed of a metal oxide selected from the group consisting of titanium, niobium, hafnium, indium, tin, and zinc oxides, and a combination of one or more of the foregoing metal oxides.

12. A photoelectronic device comprising:
the photoanode according to claim 7;
a cathode; and
an electrolyte layer formed between the photoanode and the cathode.

* * * * *